(12) United States Patent
Protopsaltis et al.

(10) Patent No.: US 9,101,489 B2
(45) Date of Patent: Aug. 11, 2015

(54) EXPANDABLE ANTERIOR LUMBAR INTERBODY FUSION DEVICE

(71) Applicant: SPINE WAVE, INC., Shelton, CT (US)

(72) Inventors: Dimitri Protopsaltis, Memphis, TN (US); Troy D. Drewry, Memphis, TN (US); Joshua Morin, Newington, CT (US); Hugues Malandain, Easton, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 14/505,938

(22) Filed: Oct. 3, 2014

(65) Prior Publication Data

US 2015/0100125 A1 Apr. 9, 2015

Related U.S. Application Data

(60) Provisional application No. 61/887,647, filed on Oct. 7, 2013.

(51) Int. Cl.
*A61F 2/44* (2006.01)
*A61F 2/46* (2006.01)
*A61F 2/30* (2006.01)

(52) U.S. Cl.
CPC ............. *A61F 2/447* (2013.01); *A61F 2/4611* (2013.01); *A61F 2002/30579* (2013.01); *A61F 2310/00023* (2013.01)

(58) Field of Classification Search
CPC ............................ A61F 2/442; A61B 17/8852
USPC ............................................ 623/17.11, 17.15
See application file for complete search history.

(56) References Cited

U.S. PATENT DOCUMENTS

| 5,609,637 | A | 3/1997 | Biedermann et al. |
| 5,665,122 | A | 9/1997 | Kambin |
| 6,045,579 | A | 4/2000 | Hochshuler et al. |
| 6,102,950 | A | 8/2000 | Vaccaro |
| 6,129,763 | A | 10/2000 | Chauvin et al. |
| 6,159,244 | A | 12/2000 | Suddaby |
| 6,432,106 | B1 | 8/2002 | Fraser |
| 6,436,140 | B1 | 8/2002 | Liu et al. |
| 6,773,460 | B2 | 8/2004 | Jackson |
| 7,108,862 | B2 | 9/2006 | Remington et al. |

(Continued)

FOREIGN PATENT DOCUMENTS

| WO | 2005120400 A2 | 12/2005 |
| WO | 2009064787 A2 | 5/2009 |
| WO | 2012009152 A2 | 1/2012 |

*Primary Examiner* — Andrew Yang
(74) *Attorney, Agent, or Firm* — Hoffmann & Baron, LLP

(57) ABSTRACT

An expandable anterior lumbar interbody fusion device comprises a deformable monolithic body having posterior and anterior ends, an upper bone contact structure and a lower bone contact structure. The body is expandable along a height axis between a first smaller height to a second larger height. The body comprises a pair of opposed side structures, each including a translatable center section being movable in a direction transverse to the height axis, a first locator arm adjacent the posterior end, a second locator arm adjacent the anterior end and a pair of formable load-bearing columns supported by the upper bone contact structure, the lower bone contact structure and the center section. The columns are not formed at the first height but are operative upon expansion of the body to the second height to form load-bearing columns along the height axis between the upper and lower bone contact structures.

28 Claims, 10 Drawing Sheets

(56) References Cited

U.S. PATENT DOCUMENTS

| | | |
|---|---|---|
| 7,220,280 B2 | 5/2007 | Kast et al. |
| 7,670,375 B2 | 3/2010 | Schaller |
| 7,846,206 B2 | 12/2010 | Oglaza et al. |
| 8,133,232 B2 | 3/2012 | Levy et al. |
| 8,267,939 B2 | 9/2012 | Cipoletti et al. |
| 8,273,122 B2 | 9/2012 | Anderson |
| 8,282,682 B2 | 10/2012 | Kirschman |
| 8,308,804 B2 | 11/2012 | Krueger |
| 8,323,342 B2 | 12/2012 | Schwab |
| 8,382,842 B2 | 2/2013 | Greenhalgh et al. |
| 8,425,570 B2 | 4/2013 | Reiley |
| 8,480,748 B2 | 7/2013 | Poulos |
| 8,641,769 B2 | 2/2014 | Malandain |
| 2003/0125739 A1 | 7/2003 | Bagga et al. |
| 2006/0058880 A1 | 3/2006 | Wysocki et al. |
| 2007/0032872 A1 | 2/2007 | Simonton et al. |
| 2007/0225807 A1 | 9/2007 | Phan et al. |
| 2007/0282443 A1 | 12/2007 | Globerman et al. |
| 2008/0114367 A1 | 5/2008 | Meyer |
| 2009/0240335 A1 | 9/2009 | Arcenio et al. |
| 2010/0174375 A1 | 7/2010 | Schaller |
| 2010/0185291 A1 | 7/2010 | Jimenez et al. |
| 2010/0292796 A1 | 11/2010 | Greenhalgh et al. |
| 2011/0137421 A1 | 6/2011 | Hansell et al. |
| 2012/0071977 A1 | 3/2012 | Oglaza et al. |
| 2012/0158143 A1 | 6/2012 | Shapiro |
| 2012/0191196 A1 | 7/2012 | Louis et al. |
| 2012/0197401 A1 | 8/2012 | Duncan et al. |
| 2012/0245691 A1 | 9/2012 | Reimels |
| 2012/0277872 A1 | 11/2012 | Kana et al. |
| 2012/0277873 A1 | 11/2012 | Kana et al. |
| 2013/0123927 A1 | 5/2013 | Malandain |
| 2013/0158668 A1 | 6/2013 | Nichols et al. |
| 2013/0261747 A1 | 10/2013 | Geisert |

| LEADING EDGE | UN-EXPANDED ANT. HEIGHT | EXPANDED ANT. HEIGHT | EXPANSION Δ |
|---|---|---|---|
| 8.8 | 15 | 19 | 4 |
| 8.8 | 15 | 18 | 3 |
| 8.8 | 15 | 17 | 2 |
| 7.8 | 13 | 17 | 4 |
| 7.8 | 13 | 16 | 3 |
| 7.8 | 13 | 15 | 2 |
| 6.8 | 11 | 15 | 4 |
| 6.8 | 11 | 14 | 3 |
| 6.8 | 11 | 13 | 2 |

FIG.4

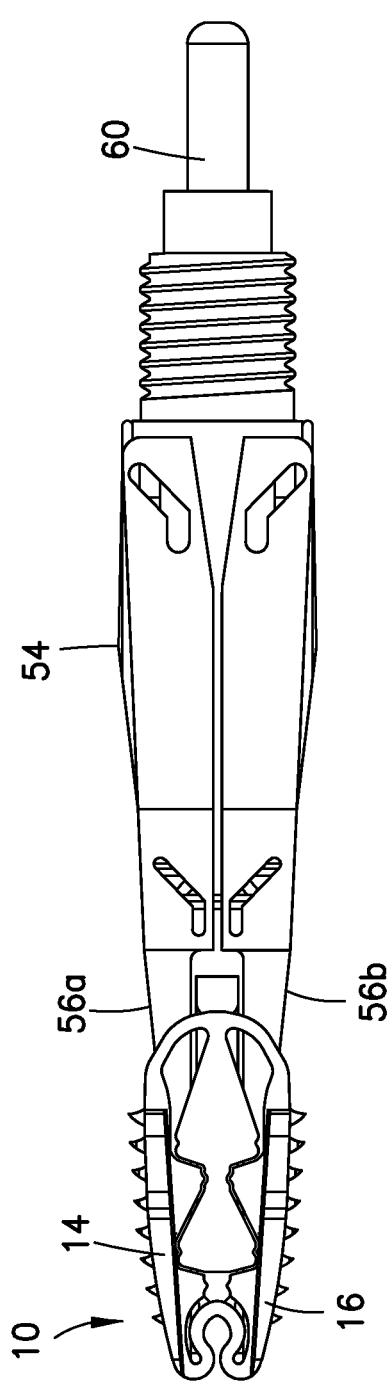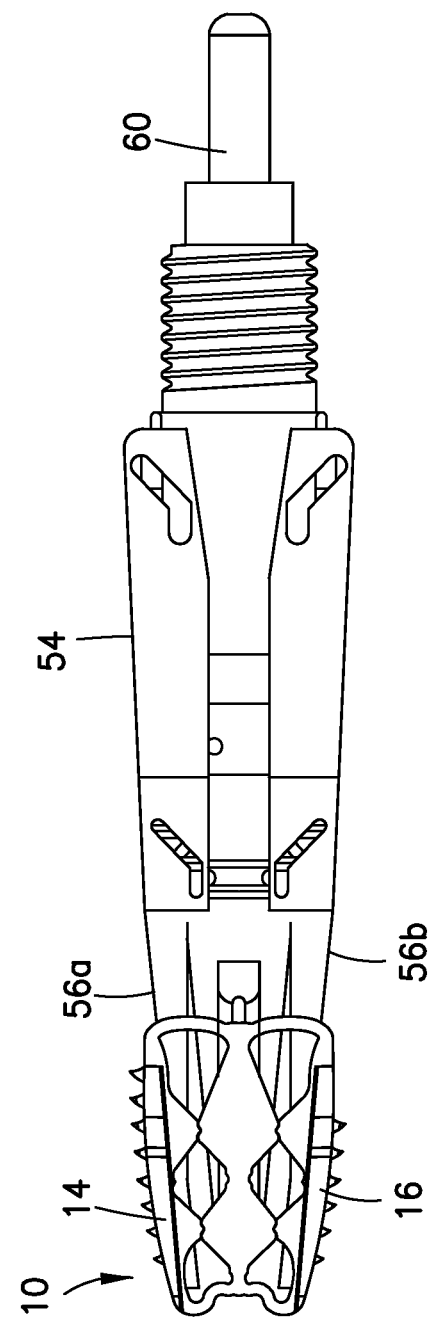

EXPANDABLE ANTERIOR LUMBAR INTERBODY FUSION DEVICE

CROSS-REFERENCE TO RELATED APPLICATION

This application claims priority to U.S. Provisional Patent Application No. 61/887,647, filed Oct. 7, 2013, the entire contents of which are incorporated by reference herein.

FIELD OF THE INVENTION

The subject invention relates generally to the field of spinal implants and more particularly to an expandable anterior lumbar interbody fusion device.

BACKGROUND OF THE INVENTION

Spinal implants such as spinal interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

There are various approaches that a surgeon may take to perform spinal fusion. Such approaches include a posterior approach, which is accessed from the back of the spine, or an anterior approach, which is accessed from the front. Other approaches which may be used include a transforaminal approach and a lateral approach, which is accessed from the side of the patient. The particular approach selected is primarily determined by the type of treatment to be administered by the surgeon. For patients that require treatment for conditions including degenerative disc disease, spinal instability or deformity, anterior lumbar interbody fusion (ALIF) has been found to be effective. The ALIF procedure and associated devices have certain advantages over other procedures. The first is that there is typically less disruption to surrounding musculature and nerves. Once access is achieved, there is a relatively open space to work in. This allows for more efficient removal of disc material thereby providing a larger potential fusion bed. The ALIF procedure also allows for a larger implant both in footprint and height, which creates better height and lordosis restoration as well as greater spinal stability.

Anterior lumbar interbody fusion requires an incision through the patient's abdomen and retraction of the surrounding muscles and abdominal contents to the side. After the affected disc is removed a structural ALIF device or implant is inserted which may be packed before, during or after insertion with a suitable bone graft material. Some types of ALIF devices are expandable so as to correct height between adjacent vertebrae. In certain of these expandable ALIF devices only the anterior end is specifically expandable, so as to produce an expansion of the disc height at the anterior side greater than the posterior side in an effort to correct lordosis. Examples of such expandable devices include U.S. Pat. No. 6,773,460, issued to Roger P. Jackson on Aug. 10, 2004, and U.S. Pat. No. 6,102,950, issued to Alex Vacarro on Aug. 15, 2000. While it is typically not desirable to increase the posterior side greater than the anterior side, it is often desirable to increase both the posterior and anterior sides an amount sufficient to not only correct disc height but to also adequately decompress neural elements.

Furthermore, it is desirable that an expandable ALIF device allow for maximum introduction of biologic bone graft material as well as for optimized openings in the inferior and superior surfaces of the ALIF device so as to maximize contact area between graft material and the endplates of the opposing vertebral bodies. Certain of the known expandable ALIF devices include expansion structure or mechanisms that tend to impede the graft loading process, particularly after expansion.

Accordingly, there is a need for an improved expandable ALIF fusion device to address these shortcomings.

SUMMARY OF THE INVENTION

It is an object of the invention to provide an improved expandable anterior lumbar interbody fusion device. In accordance with a particular aspect, the expandable anterior lumbar interbody fusion device a comprises a monolithic device to be inserted into the anterior lumbar interbody disc space in a shorter, unexpanded size and then deployed in the disc space into a taller, expanded implant. The expansion is created mechanically with an instrument through plastic deformation of the implant material during transition from the shorter configuration to the taller configuration. Once final expansion and implant height is reached, the implant is locked into place with a tab and recess to maintain this height. Implant geometry is such that implant structural endplates match the convexity and size of the mating vertebral body surfaces. This anatomical fit ensures proper bony engagement to provide biomechanical support of the bony surfaces to resist implant subsidence during expansion. In addition, implant configurations can be designed to include different angles of lordosis built into the geometry to allow for spinal alignment and deformity correction to be created or maintained during expansion to improve sagittal balance of the spine. Expansion is produced via instrumentation in a parallel fashion to increase both the anterior and posterior disc height to provide adequate decompression on the neural elements. Once spinal alignment and deformity correction is accomplished through implant expansion, spinal fusion between vertebral bodies can be conducted. The implant has been designed with an "open" architecture to maximize the amount of biologic graft material that can be placed into the implant as well as optimized windows in the inferior and superior implant endplates to maximize fusion surface area contact between the endplate and graft material. Finally, optional supplemental fixation may be provided that allows for fixation of the post-expanded implant to the vertebral bodies above and below the disc space.

DESCRIPTION OF THE FIGURES

FIG. 4 is a table showing examples of the potential expandability of the device of FIG. 1A.

FIG. 5B is a side elevation view of the device and instrument of FIG. 5A with the instrument portion attached to the device before expansion.

FIG. 5C is a side elevation view of the device and instrument of FIG. 5B with the device having been expanded by the instrument portion to the form of FIG. 1B.

DESCRIPTION OF THE EMBODIMENTS

Figure 1A:
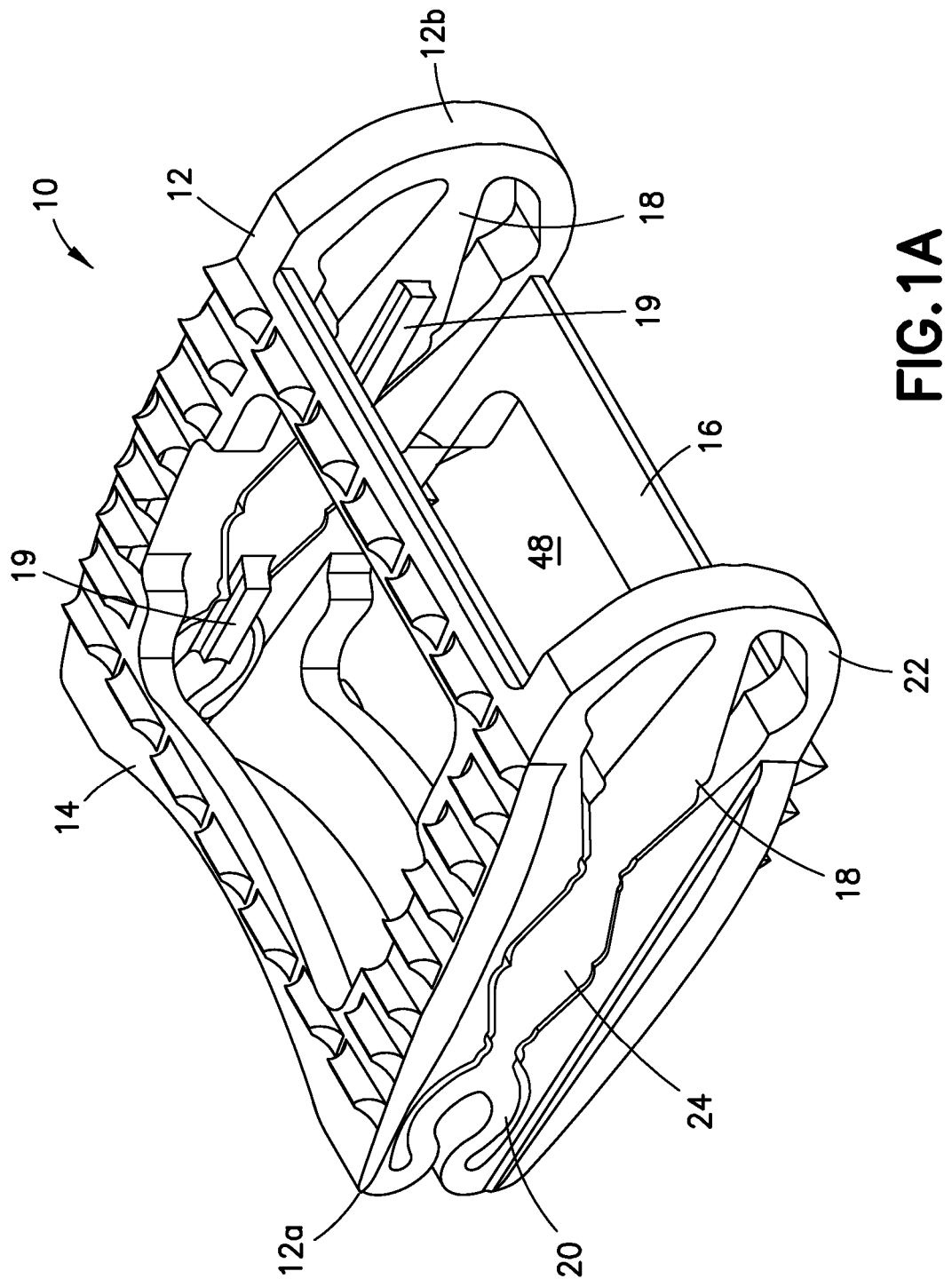
FIGS. 1A and 1B are top perspective views of an anterior lumbar interbody fusion device in accordance with one embodiment, showing the device respectively in collapsed unexpanded form and fully expanded form.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Described herein is an anterior lumbar interbody fusion device 10 for insertion into the intradiscal space between opposing vertebrae from the anterior approach. In particular, the described device 10 is suitable as a spinal fusion implant that is introduced at a lower profile and expanded along a height axis to a higher profile at the implantation site. The device 10 is monolithic and expanded by deformation, preferably plastic deformation, of the monolithic body. The device 10 incorporates partial support components that become aligned during the process of deformation (and expansion) and cooperate to form a complete support component that typically supports a major portion of stress applied to the implant. Further details of the expansion of the monolithic device 10 and its expansion characteristics are more fully described in commonly owned U.S. Pat. No. 8,641,769, issued to Hugues Malandain on Feb. 4, 2014 (the '769 patent), and incorporated in its entirety by reference herein.

Figure 1B:
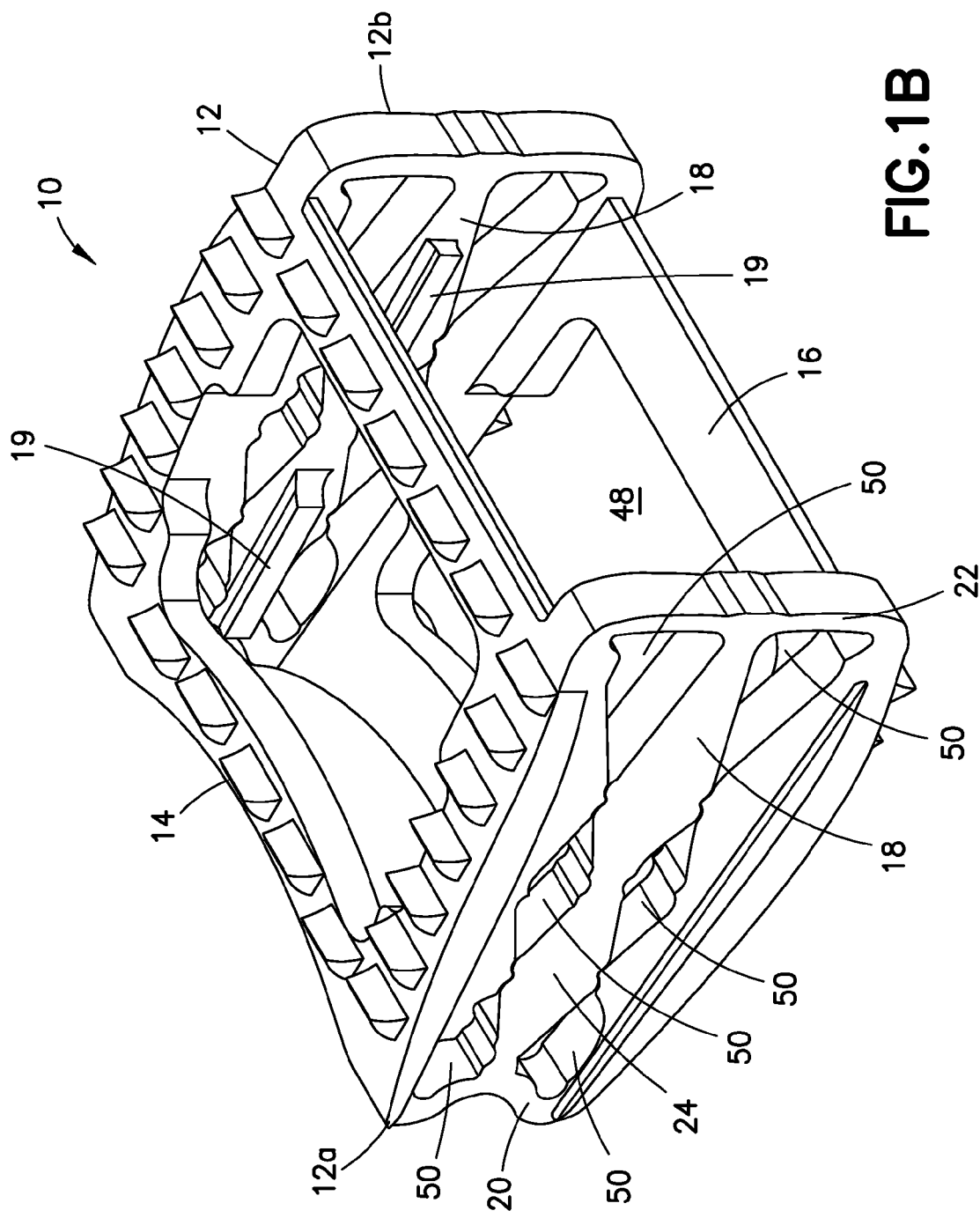

Turning now to the drawing figures, details of device 10 may be more fully understood. FIG. 1A shows device 10 in its smaller, low-profile profile configuration as might be utilized during initial introduction of the device 10 into a treatment site. As shown in FIGS. 1A and 1B, device 10 comprises a deformable monolithic body 12 having a posterior end 12a and anterior end 12b, an upper bone contact structure 14, a lower bone contact structure 16 and a pair of spaced apart side structures 18 joining upper bone contact structure 14 and lower bone contact structure 16. FIG. 1B shows device 10 after complete expansion and permanent deformation of the device.

Figure 2A:
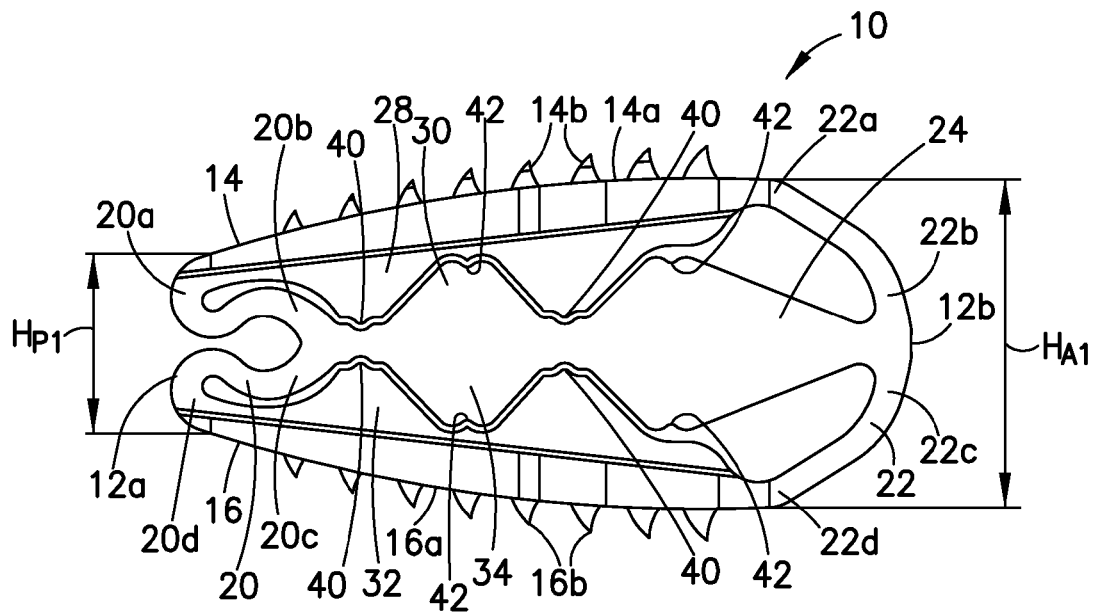
FIGS. 2A and 2B are side elevation views of the collapsed and expanded forms of the device respectively shown in FIGS. 1A and 1B.
Figure 2B:
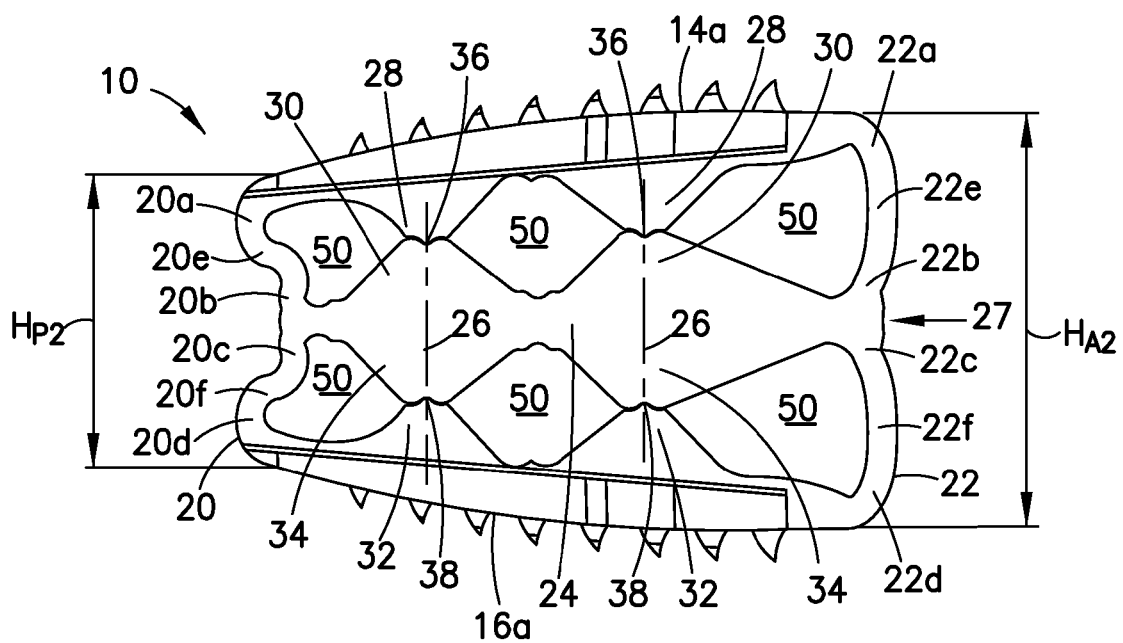

The device 10, as further depicted in FIGS. 2A and 2B, includes an upper outer bone contact surface 14a defined by the underlying upper bone contact structure 14, and a lower outer bone contact surface 16a defined by the underlying lower bone contact structure 16. Upper outer bone contact surface 14a and lower outer bone contact surface 16a are preferably formed as convex surfaces so as to match the anatomic convexity and size of the cartilaginous endplates of the respective mating vertebral body surfaces. This anatomical fit ensures proper bony engagement to provide biomechanical support of the bony surfaces to resist device subsidence during expansion. The upper and lower bone contact surfaces 14a and 16a also preferably include a number of serrations 14b and 16b serving a bone anchoring function. These functional anchors may assist in holding the device 10 in position during implantation or may hold the device 10 in position after implantation. Other forms of functional bone anchoring components, e.g. fins, spikes, hooks, etc., may be substituted as desired. As will be further described, the height of posterior end 12a is less than the height of anterior end 12b, with upper and lower bone contact structures 14, 16 inclining toward each other to thereby define a wedge-shaped lordotic configuration for anterior placement. It should be appreciated, however, that only one of the upper bone contact structure 14 or lower bone contact structure 16 may be angled toward the other. In an example where device 10 is symmetrical about its longitudinal centerline, each of upper and lower bone contact structures 14, 16 is angled approximately the same amount from the centerline of device 10. As such, where device 10 is provided to have a 15 degree lordotic angle, upper bone contact structure 14 is 7.5 degrees from the centerline and the lower bone contact structure is 7.5 degrees from the centerline as well. The included angle between upper and lower bone contact structures 14, 16 is 15 degrees, in this example.

Referring still to FIGS. 1A and 1B as also to FIGS. 2A and 2B, further details of the side structures 18 are described. As each of the side structures 18 is identical, only the elements of one side structure 18 will be described. Side structure 18 comprises a first locator arm 20 adjacent the posterior end 12a of body 12, a second locator arm 22 adjacent the anterior end 12b and a translatable center section 24 disposed between the upper bone contact structure 14 and the lower bone contact structure 16. Center section 24 is movable in a direction generally transverse to the height axis of device 10 between the upper bone contact structure 14 and the lower bone contact structure 16.

First locator arm 20 is joined at posterior end 12a to upper bone contact structure 14 at deformable joint 20a, to center section 24 at two deformable joints 20b and 20c, and to lower bone contact structure 16 at deformable joint 20d. Second locator arm 22 is joined at anterior end 12b to upper bone contact structure 14 at deformable joint 22a, to center section 24 at two deformable joints 22b and 22c, and to lower bone contact structure 16 at deformable joint 22d. The deformable joints 20a-d and 22a-d may be formed by providing a reduced cross-sectional area that provides a region of reduced strength and localized bending and, with appropriate materials, plastic deformation. An upper portion 20e of first locator arm 20 between upper bone contact structure 14 and center section 24, and a lower portion 20f of first locator arm 20 between center section 24 and lower bone contact structure 16 are likewise deformable during the expansion process, as seen in FIG. 2B. An upper portion 22e of second locator arm 22 between upper bone contact structure 14 and center section 24, and a lower portion 22f of second locator arm 20 between center section 24 and lower bone contact structure 16 are similarly deformable during the expansion process. The upper and lower first locator arm portions 20e, 20f and the upper and lower second locator arm portions 22e, 22f are preferably formed such that the deformation upon expansion is plastic.

Referring particularly to FIGS. 2A and 2B, each side structure 18 further includes a pair of formable load-bearing columns 26 that span the distance between upper bone contact surface 14 and lower bone contact surface 16 along the height axis. Columns 26 are disposed between first locator arm 20 and second locator arm 22 along the anterior to posterior direction. While it is preferable that each side structure 18 includes at least two load-bearing columns 26, it should be appreciated that more than two columns 26 may also be provided. Each of the columns 26 includes a pair of upper partial columns 28 and 30 a pair of lower partial columns 32 and 34. Upper partial column 28 is supported by upper bone contact structure 14 and projects downwardly toward center section 24. Upper partial column 30 is supported by center section 24 and projects upwardly toward upper bone contact structure 14. Lower partial column 32 is supported by lower bone contact structure 16 and projects upwardly toward the center section 24. Lower partial column 34 is supported by center section 24 and projects downwardly toward lower bone contact structure 16. Load-bearing columns 26 are not formed when device 10 is in the collapsed condition as illustrated in FIGS. 1A and 2A. As further seen in FIGS. 1A and 1B and also in FIGS. 3A and 3B, each of said side structures 18 includes a rail 19 extending along at least a portion of center section 24 and projecting inwardly into the interior 44 of body 12. Rails 19 are provided to engage with a cooperatively formed track in the device expansion instrument, as will be described.

As device 10 is expanded, as will be described, center section 24 is translated relative to upper bone contact structure 14 and lower bone contact structure 16 in a direction transverse to the height axis, as shown by arrow 27 in FIG. 2B. Upon such expansion, partial columns 28, 30 and 32, 34 move into alignment and ultimately latch together as shown in FIG. 2B by latching structure 36 and 38 at the apices of the partial columns 28, 30 and 32, 34. In one arrangement, latching structure 36, 38 may comprise a tab 40 on one of the partial columns and a recess 42 on the opposite, mating partial column, as depicted in FIG. 2A. Tabs 40 and recesses 42 serve as cooperative engagement surfaces that latch to form the complete load-bearing columns 26 upon expansion of device 10. During such expansion, upper bone contact structure 14 is moved along the height axis in a manner away from but parallel to lower bone contact structure 16 as a result of the deformation of the deformable joints 20a-d and 22a-d as well as the deformation of the upper and lower first locator arm portions 20e, 20f and the upper and lower second locator arm portions 22e, 22f. As such, the increase in expansion of device 10 at anterior end 12b from height $H_{A1}$ to height $H_{A2}$ is the same as the increase in expansion at the posterior end 12a from height $H_{P1}$ to height $H_{P2}$. Furthermore, as the deformation of the deformable joints 20a-d and 22a-d and the upper and lower first locator arm portions 20e, 20f and the upper and lower second locator arm portions 22e, 22f is preferably plastic the increase in height of device 10 is substantially maintained after expansion not only by the formed load-bearing columns 26, but also by the plastically deformed first and second locator arms at the posterior and anterior ends 12a and 12b, respectively.

Figure 3A:
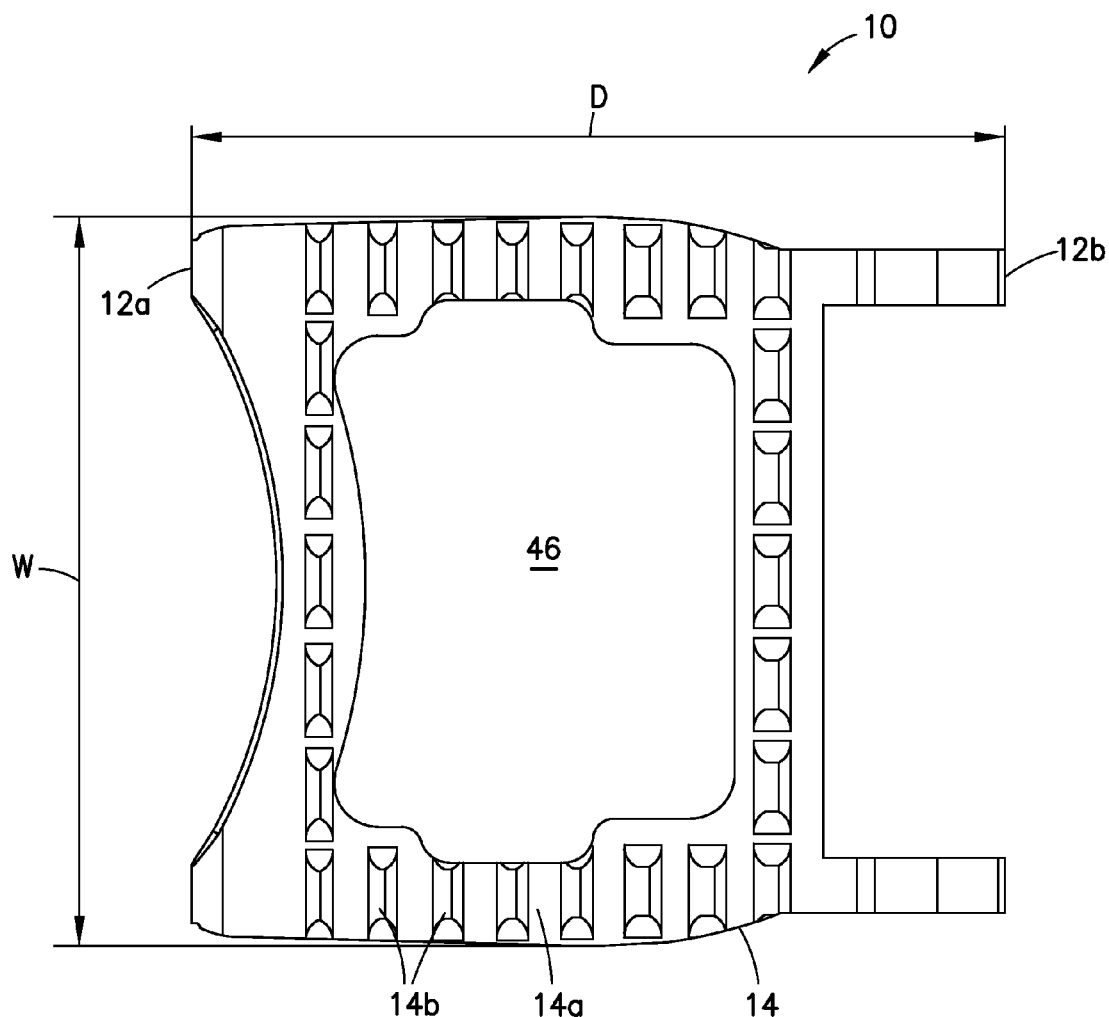
FIGS. 3A, 3B and 3C show, respectively, top, front end and rear end views of the collapsed device of FIG. 1A.
Figure 3B:
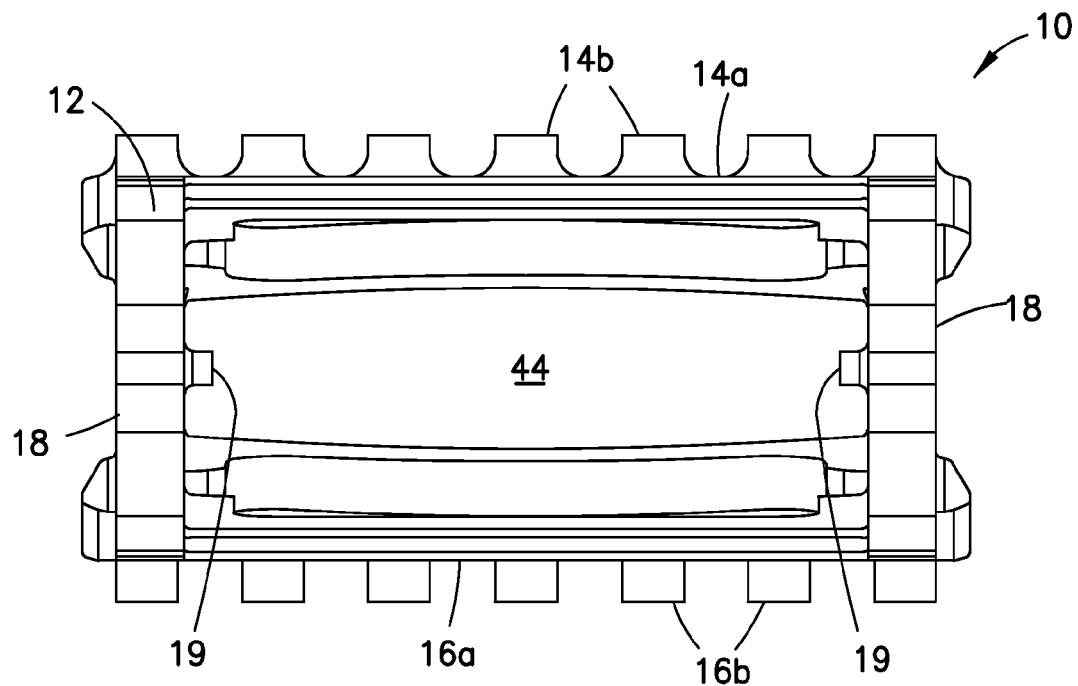
Figure 3C:
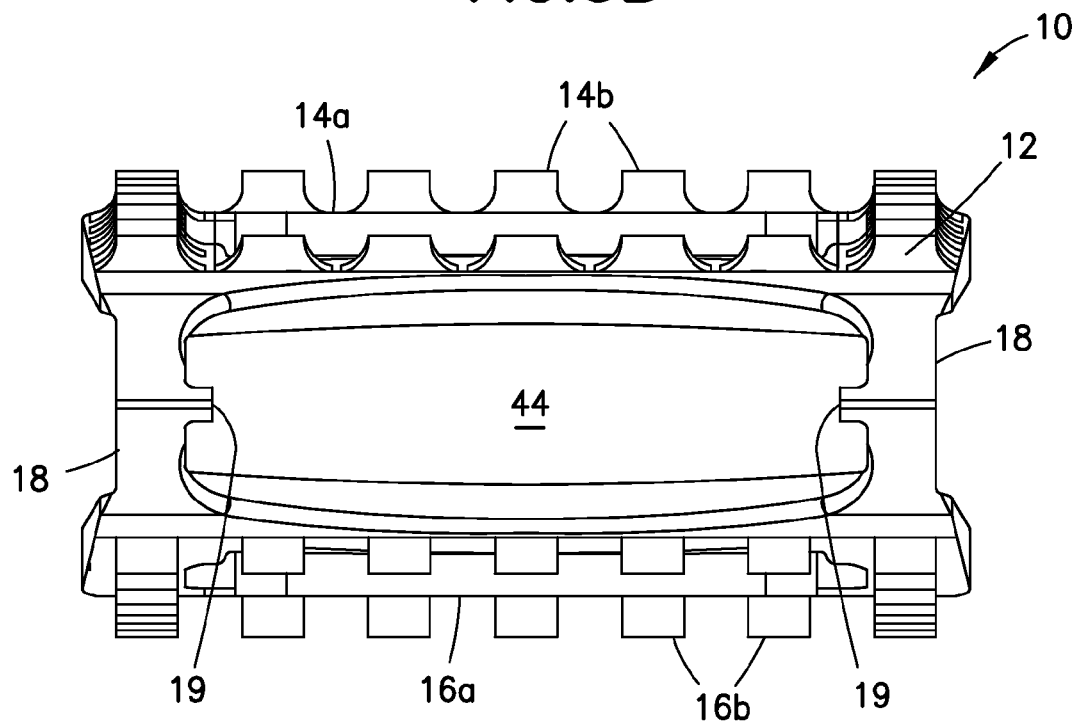

With reference now also to FIGS. 3A-C, the open architecture of device 10 may be more fully understood. Upper bone contact structure 14, lower bone contact structure 16 and spaced apart side structures 18 define an unobstructed interior 44 within device 10 that extends through both the posterior end 12a and anterior end 12b. Upper bone contact structure 14 includes an opening 46 extending therethrough and lower bone contact structure 16 includes an opening 48 (FIG. 1B) extending therethrough. Side structures 18 each include openings 50 extending therethrough. All of the openings 46, 48 and 50 communicate directly with interior 44. In one arrangement, opening 46 through upper bone contact structure 14 comprises approximately 50% of the area of upper outer bone contact surface 14a. Similarly, opening 48 through lower bone contact structure 16 comprises approximately 50% of the area of lower bone contact surface area 16a. Such an opening to surface area ratio has been found to provide a sufficiently large enough area so as to maximize contact between graft material introduced into interior 44 and the endplates of the opposing vertebral bodies while providing sufficient structural surface area to minimize subsidence. In addition, in one arrangement the openings 50 through side structures 18 comprise approximately 30% of the outer surface areas of side structures 18. Such an arrangement contributes to the open architecture of device 10 and the flow of bone graft material therethrough. It should be appreciated however that the ratio of the openings to surface areas of device 10 may be varied depending upon different circumstances and applications.

Turning now also to the table of FIG. 4, a number of examples are provided relating to the expandability of the design of device 10. For example, a device 10 may have a width W, a depth D, an unexpanded leading edge height $H_{P1}$ at the posterior end 12a and an unexpanded trailing edge height $H_{A1}$ at the anterior and 12b, as depicted in FIGS. 2A, 2B and 3A. The width W is defined as the maximum lateral distance between the outer surfaces of side structures 18, the depth D is defined as the maximum distance between the distal and proximal edges of device 10 at the posterior and anterior ends 12a, 12b. The maximum height $H_{A2}$ of device 10 is defined as the maximum distance of the expanded device 10 between upper outer bone contact surface 14a and lower outer bone contact surface 16a at anterior end 12b.

A set of three small devices 10, for example, may be provided, each having a width W of 26 mm and a depth D of 24 mm. Each of the three devices 10 may have an unexpanded leading edge height $H_{P1}$ of 6.8 mm and an unexpanded trailing edge height $H_{A1}$ of 11 mm, thereby providing a lordotic configuration. One of the three devices 10 may be configured to expand to 2 mm for an expanded height $H_{A2}$ of 13 mm, the second device 10 may be configured to expand 3 mm for an expanded height $H_{A2}$ of 14 mm, and a third device may be configured to expand 4 mm for an expanded height $H_{A2}$ of 15 mm, as set forth in the table of FIG. 4. As such, different angles of lordosis may be provided by the different devices. A similar set of medium and large devices 10 may be provided, the medium devices 10 each having a width W of 28 mm and a depth D of 26 mm and the large devices 10 each having a width W of 30 mm and a depth the of 28 mm. Further examples of devices 10 having unexpanded leading edge heights $H_{P1}$ of 7.8 mm and 8.8 mm are provided in the table of FIG. 4. It should be appreciated that the examples set forth herein are illustrative and that other sizes and dimensions of devices 10 may also be provided.

Kits of any of the devices discussed above may be provided where the devices are selected to include a variety of expanded heights or selected to have differing collapsed heights, or differing widths or depths, or are selected to include differing lordotic angles between the posterior and anterior ends. Each of these kits may further include instrumentation to introduce the devices into a chosen site in the intradiscal space between opposing vertebral bodies.

Figure 5A:
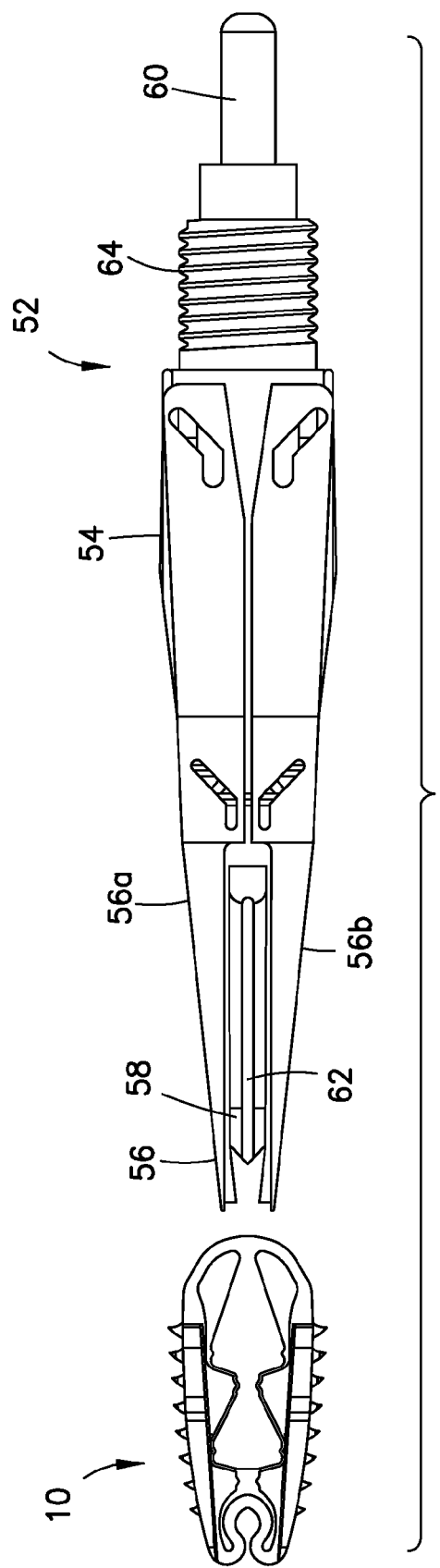
FIG. 5A is a side elevation exploded view of the collapsed device of FIG. 1A and a portion of an instrument for use in inserting and expanding the collapsed device.

Turning now to FIGS. 5A-C, one arrangement of instrumentation for use in inserting device 10 into the intradiscal space and expanding device 10 therein is described. Such instrumentation 52 may include a modular tool portion 54 including an expandable tip 56 specifically configured for receipt into interior 44 of device 10. Tip 56 includes a pair of plates 56a and 56b that are movably separated by an axially translatable wedge 58. Wedge 58 is coupled to an axially movable shaft 60 that in turn is coupled to an actuator (not shown) that may drive shaft 60 by means of a rotatable screw mechanism or any other suitable mechanism. Wedge 58 further comprises a pair of tracks 62 recessed on opposite sides of wedge 58 and extending for an extent laterally along a length of wedge 58. Tracks 62 are sized and configured to cooperatively engage respective rails 19 projecting into the interior 44 of body 12. The engagement between rails 19 and track 62 provides support to center section 24 during expansion in a manner to allow center section 24 to translate substantially perpendicularly to the height axis of body 12. Tool portion 54 may be suitably separably connected to the actuator by a threaded section 64. As such, a variety of tool portions 54 may be provided in the kit, each of which includes an expandable tip 56 particularly configured for a selected device 10. As shown in FIG. 5B, tool portion 54 is suitably attached to a selected device 10 by insertion of expandable tip 56 into interior 44. Plates 56a and 56b contact respective interior surfaces of upper bone contact structure 14 and lower bone contact structure 16 upon attachment. As wedge 58 is driven axially by the actuator by way of movement of shaft 60 plates 56a and 56b are moved apart thereby moving apart upper bone contact structure 14 and lower bone contact structure 16 along the height axis to expand device 10, as described hereinabove.

Device 10 may comprise a suitable metallic or polymeric material. Suitable biocompatible metallic materials include pure titanium, tantalum, cobalt-chromium alloys, titanium alloys (e.g., nickel titanium alloys and tungsten titanium alloys), and stainless steel alloys. Suitable polymeric materials include members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. Ceramic materials such as aluminum oxide or alumina, zirconium oxide or zirconia, compact of particulate diamond, or pyrolytic carbon may be included in such polymers.

Having described the structure and function of device 10 herein, the method of using device 10 in an anterior lumbar interbody fusion is now described. An incision is made through the patient's abdomen and the surrounding muscles and abdominal contents are retracted to the side to form an open surgical access corridor. The affected disc is removed to provide a proper space between opposing vertebral bodies. The surgeon may determine the appropriate size of device 10 for insertion by using a suitable trialing device. Once the appropriate size is determined, a desired device 10 is selected from the kit and suitably attached to a selected tool tip 56. The device 10 is inserted into the disc space by tool portion 54 through manipulation of the actuator by the surgeon. Once introduced into the disc space, device 10 is expanded as described herein. After device 10 is expanded, all or a portion of the interior 44 of device 10 as well as the disc space surrounding device 10 may be filled in situ with a suitable bone graft material containing bone growth promoting substances. Other osteogenic materials or therapeutic compositions may also be used, such materials and compositions being more fully described in the '769 patent, incorporated herein by reference. Supplemental fixation may then be provided for fixation of the expanded device 10 to the vertebral bodies above and below the disc space.

It should now be appreciated that the expandable anterior lumbar interbody fusion device 10 described herein may be inserted into a smaller intradiscal disc space than a non-expandable fusion device, thereby minimizing damage to bony structure that may be associated with heavy impaction. Additionally, expansion of device 10 provides indirect decompression of adjacent neural elements while maintaining appropriate lordosis of the patient's spine. The expandable inclined configuration of upper bone contact structure 14 and lower bone contact structure 16 allows for deformity correction of the spine as well as sagittal balance restoration while providing both posterior and anterior disc space distraction. Furthermore, the open architecture of device 10, particularly of the upper and lower bone contact structures 14, 16, allows for preparation of vertebral endplates through the device 10 after insertion, which may potentially reduce subsidence. Such openness of device 10 also allows for packing of more bone graft material.

Figure 6:
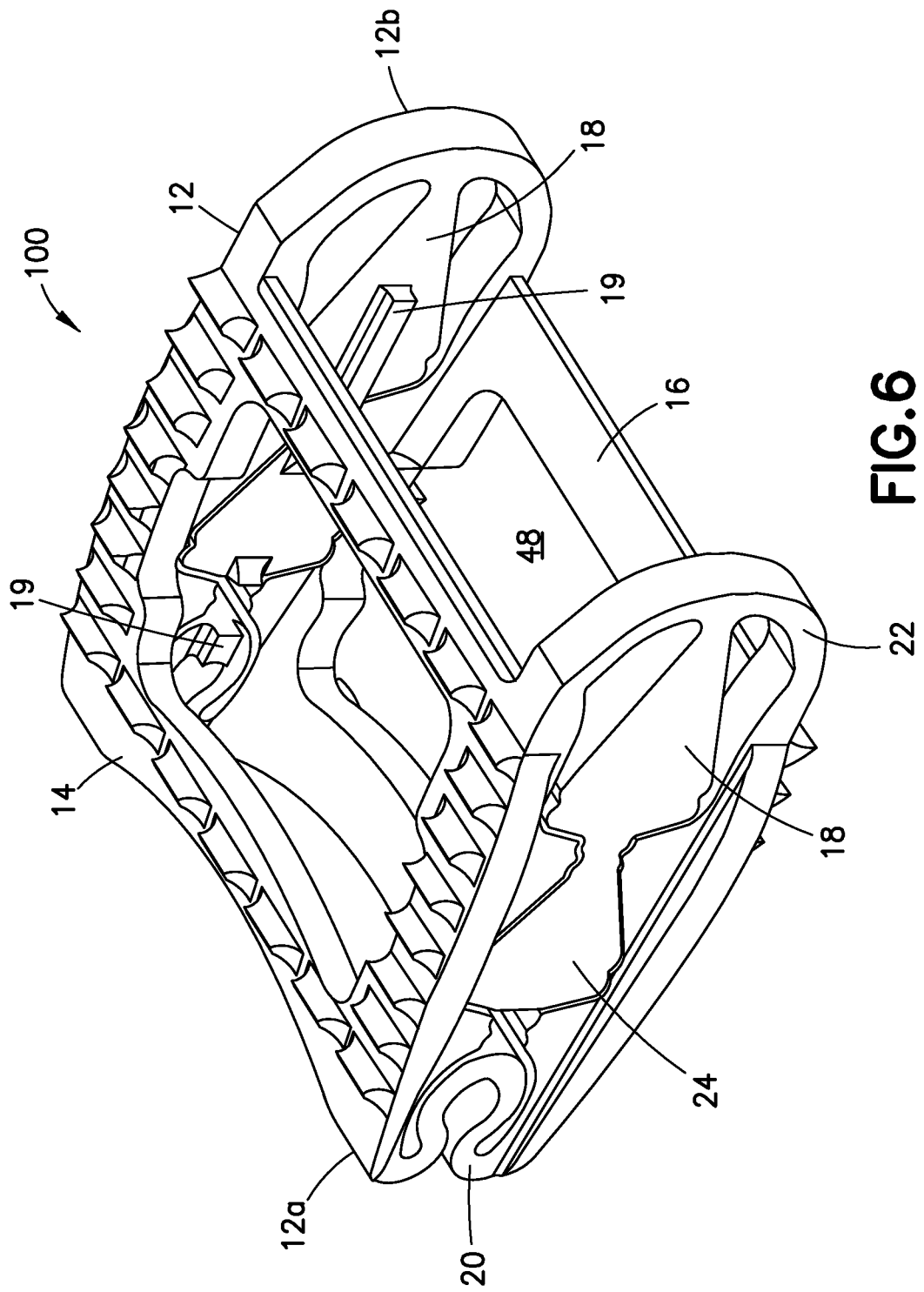
FIG. 6 is a top perspective view of an anterior lumbar interbody fusion device in accordance with another embodiment, showing the device in collapsed unexpanded form.
Figure 7A:
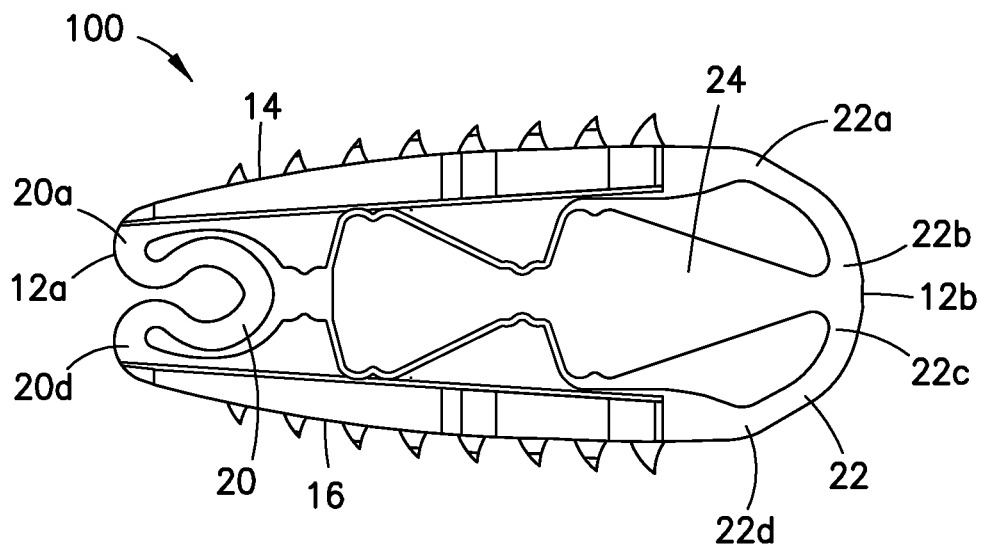
FIGS. 7A and 7B are side elevation views of the collapsed and expanded forms of the device shown in FIG. 6.
Figure 7B:
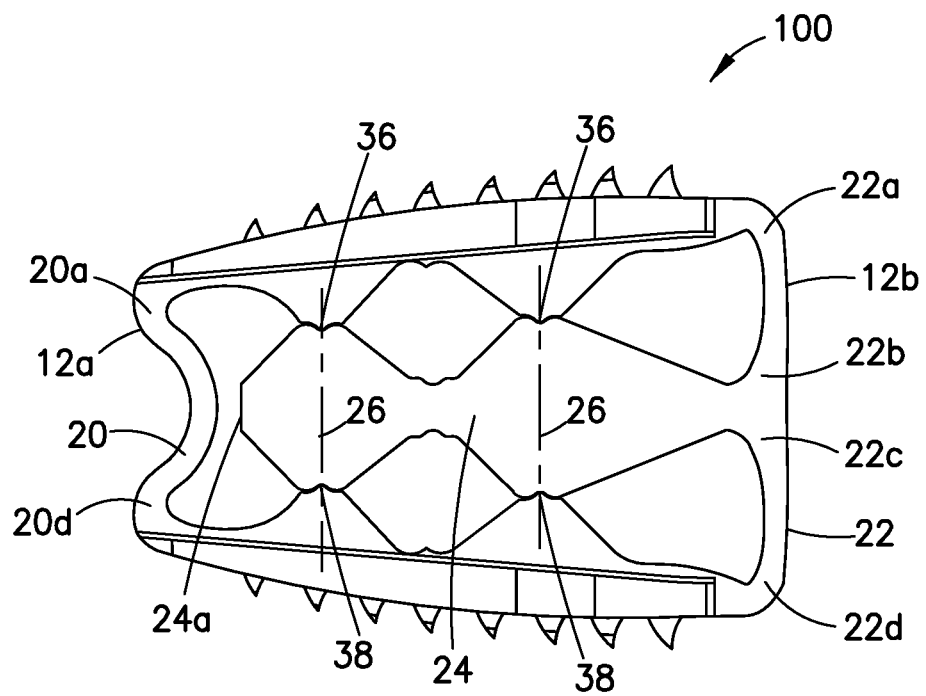

Turning now to FIGS. 6 and 7A and 7B, another embodiment of an anterior lumbar interbody fusion device 100 is shown. Device 100 is identical to previously described device 10, except that center section 24 is not joined to and is spaced from at least one of the first locator arm 20 or the second locator arm 20. Preferably, center section 24 is detached from first locator arm 20 at the posterior end 12a of body 12. Such detachment allows center section 24 to translate more freely without influencing deformation of first locator arm 20 while center section 24 is being positioned to form the pair of formable load-bearing columns 26 and the latching of latching structure 36 and 38. In addition, the greater freedom of movement of center section 24 together with the support provided by rails 19 and expansion instrument tracks 62 further enables movement of upper bone contact structure 14 and lower bone contact structure 16 during expansion in a substantially parallel manner in the height axis. As shown in FIG. 7B, upon full expansion of device 100 the free end 24a of center section 24 remains spaced from first locator arm 20.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An expandable anterior lumbar interbody fusion device, comprising:

a deformable monolithic body having a posterior end and an anterior end, an upper bone contact structure having an upper opening therethrough, a lower bone contact structure having a lower opening therethrough, a pair of spaced apart side structures joining said upper bone contact structure and said lower bone contact structure, each of said side structures having an opening therethrough and defining with said upper bone contact structure and said lower bone contact structure an open interior of said body, said upper opening, said lower opening and said openings through said side structures for communicating with said interior, said body being expandable along a height axis between the first smaller height to a second larger expanded height, each of said side structures including:

a translatable center section between said upper bone contact structure and said lower bone contact structure, said center section having a posterior end and an anterior end, said center section being movable in a direction transverse to said height axis;

a first locator arm adjacent the posterior end, said first locator arm being joined to said upper bone contact structure, said lower bone contact structure and said center section at the respective posterior ends by a deformable joint, one or more of said deformable joints being configured to be plastically deformable, said first locator arm being plastically deformable between said deformable joints;

a second locator arm adjacent the anterior end, said second locator arm being joined to said upper bone upper bone contact structure, said lower bone contact structure and said center section at the respective anterior ends by a deformable joint, said second locator arm being deformable between said deformable joints; and a pair of formable load-bearing columns supported by said upper bone contact structure, said lower bone contact structure and said center section that are not formed at said first height and are operative upon expansion of said body to said second height to form said load-bearing columns along the height axis that spans the distance between said upper bone contact structure and said lower bone contact structure.

2. The device of claim 1, wherein each of said formable columns comprises an upper partial column projecting from one of said upper bone contact structure or said center section toward the other of said upper bone contact structure or said center section, the other of said upper bone contact structure or said center section including an upper cooperative engagement surface.

3. The device of claim 2, wherein said formable columns each include a latching structure between said upper partial column and said upper cooperative engagement surface.

4. The device of claim 3, wherein said latching structure comprises a tab on one of said upper partial column or said upper cooperative engagement surface and a recess on the other of said upper partial column or said upper cooperative engagement surface.

5. The device of claim 4, wherein each of said formable columns comprises a lower partial column projecting from one of said lower bone contact structure or said center section toward the other of said lower bone contact structure or said center section, the other of said lower bone contact structure or said center section including a lower cooperative engagement surface.

6. The device of claim 5, wherein said formable columns each include a latching structure between said lower partial column and said lower cooperative engagement surface.

7. The device of claim 6, wherein said latching structure comprises a tab on one of said lower partial column or said lower cooperative engagement and a recess on the other of said lower partial column or said lower cooperative engagement surface.

8. The device of claim 1 wherein said second locator arm of each side structure is plastically deformable between said deformable joints.

9. The device of claim 8, wherein said second locator arm of each side structure is plastically deformable between said deformable joints.

10. The device of claim 1, wherein said body has a maximum height along the height axis defined by the maximum distance between an outer surface of said upper bone contact structure and an outer surface of said lower bone contact structure.

11. The device of claim 10, wherein said body is configured to provide said maximum height at the anterior end of said body.

12. The device of claim 11, wherein the height of said posterior end is less than said maximum height, said outer surface of one of said upper bone contact structure or said lower bone contact structure inclines toward the other of said upper bone contact structure or said lower bone contact structure thereby defining a wedge-shaped lordotic configuration.

13. The device of claim 12, wherein said outer surface of both said upper bone contact structure and said lower bone contact structure incline from said anterior end to said posterior end toward each other.

14. The device of claim 1, wherein said outer surface of both said upper bone contact structure and said lower bone contact structure are convex between said anterior end and said posterior end.

15. The device of claim 10, wherein said body has a width defined by the maximum distance between an outer surface of said side structures, said width being greater than said maximum height of said body.

16. The device of claim 1, wherein said upper opening through said upper bone contact structure comprises approximately 50% of the surface area of said outer surface of said upper bone contact structure.

17. The device of claim 16, wherein the area of said opening through each of said side structures comprises approximately 30% of the surface area of each said side structure.

18. The device of claim 16, wherein said lower opening through said lower bone contact structure comprises approximately 50% of the surface area of said outer surface of said lower bone contact structure.

19. The device of claim 1, wherein said upper bone contact structure and said lower bone contact structure move apart during expansion along the height axis substantially parallel to each other while said center section moves transversely thereto.

20. The device of claim 1, wherein each of said side structures includes a rail extending along at least a portion of said center section and projecting inwardly into said interior of said body.

21. The device of claim 1, wherein said body comprises titanium.

22. An expandable anterior lumbar interbody fusion device, comprising:
a deformable monolithic body having a first end and a second end, an upper bone contact structure having an upper opening therethrough, a lower bone contact structure having a lower opening therethrough, a pair of spaced apart side structures joining said upper bone contact structure and said lower bone contact structure, each of said side structures having an opening therethrough and defining with said upper bone contact structure and said lower bone contact structure an open interior of said body, said upper opening, said lower opening and said openings through said side structures for communicating with said interior, said body being expandable along a height axis between the first smaller height to a second larger expanded height, said first end being a posterior end of said body and said second end being an anterior end of said body, and the height of the unexpanded body at the anterior end being greater than the height at said posterior end, each of said side structures including:
a translatable center section between said upper bone contact structure and said lower bone contact structure, said center section having a first end and a second end, said center section being movable in a direction transverse to said height axis;
a first locator arm adjacent the first end, said first locator arm being respectively joined to said upper bone contact structure and said lower bone contact structure at the first end by a deformable joint, said first locator arm being deformable between said deformable joints, said first locator arm being further joined to said center section at the posterior end by a deformable joint facing said upper bone contact structure and by a deformable joint facing said lower bone contact structure, said first locator arm being deformable between said respective deformable joints;

a second locator arm adjacent the second end, said second locator arm being joined to said upper bone upper bone contact structure, said lower bone contact structure and said center section at the respective second ends by a deformable joint, said second locator arm being deformable between said deformable joints; and a pair of formable load-bearing columns supported by said upper bone contact structure, said lower bone contact structure and said center section that are not formed at said first height and are operative upon expansion of said body to said second height to form said load-bearing columns along the height axis that spans the distance between said upper bone contact structure and said lower bone contact structure.

23. The device of claim 22, wherein said first locator arm is plastically deformable between said respective deformable joints.

24. A kit of parts for use in anterior lumbar interbody fusion, comprising:

a plurality of expandable anterior lumbar interbody fusion devices, each having a posterior end, an anterior end, an open interior and an unexpanded height at the anterior end greater than an unexpanded height at the posterior end, the unexpanded height at the posterior end of each of said devices being the same, the expanded height of each of said devices at the anterior end being different; and an instrument adapted to extend into the interior of each of said devices and to attach to a selected one of said devices, insert said selected device into a disc space between opposing vertebral bodies of a spine and expand said selected device therein, wherein each of said plurality of devices includes a rail extending between said posterior end and said anterior end and projecting into the interior of each of said devices, and wherein said instrument has a track sized and configured to engage said rail of each of said devices to provide support during expansion.

25. The kit of parts of claim 24, wherein each of said plurality of devices is expandable at the posterior end the same distance as the anterior end.

26. A kit of parts for use in anterior lumbar interbody fusion, comprising:

a plurality of expandable anterior lumbar interbody fusion devices, each having a posterior end, an anterior end, an open interior and an unexpanded height at the anterior end greater than an unexpanded height at the posterior end, the unexpanded height at the posterior end of each of said devices being the same, the unexpanded height at the anterior end of each of said devices being the same, and the expanded height of each of said devices at the anterior end being different; and an instrument adapted to extend into the interior of each of said devices and to attach to a selected one of said devices, insert said selected device into a disc space between opposing vertebral bodies of a spine and expand said selected device therein.

27. The kit of parts of claim 26, wherein each of said plurality of devices includes a rail extending between said posterior end and said anterior end and projecting into the interior of each of said devices, and wherein said instrument has a track sized and configured to engage said rail of each of said devices to provide support during expansion.

28. A kit of parts for use in anterior lumbar interbody fusion, comprising:

a plurality of expandable anterior lumbar interbody fusion devices, each having a posterior end, an anterior end, an open interior and an unexpanded height at the anterior end greater than an unexpanded height at the posterior end, the unexpanded height at the posterior end of each of said devices being the same, the expanded height of each of said devices at the anterior end being different; and an instrument adapted to extend into the interior of each of said devices and to attach to a selected one of said devices, insert said selected device into a disc space between opposing vertebral bodies of a spine and expand said selected device therein, said instrument comprising a set of different modular portions each having an expandable tip adapted to be selectively attached to different ones of said selected devices.

* * * * *